(12) United States Patent
Bartoszyk et al.

(10) Patent No.: US 7,479,492 B2
(45) Date of Patent: Jan. 20, 2009

(54) USE COMBINED 5-HT$_{1A}$ AGONISTS AND SELECTIVE SEROTONIN REUPTAKE INHIBITORS

(75) Inventors: Gerd Bartoszyk, Weiterstadt (DE); Ewen Sedman, Alresford (GB)

(73) Assignee: Merck Patent GmbH, Darmstadt (DE)

( * ) Notice: Subject to any disclaimer, the term of this patent is extended or adjusted under 35 U.S.C. 154(b) by 316 days.

(21) Appl. No.: 10/432,047

(22) PCT Filed: Nov. 2, 2001

(86) PCT No.: PCT/EP01/12686

§ 371 (c)(1), (2), (4) Date: May 19, 2003

(87) PCT Pub. No.: WO02/39989

PCT Pub. Date: May 23, 2002

(65) Prior Publication Data

US 2004/0014771 A1    Jan. 22, 2004

(30) Foreign Application Priority Data

Nov. 20, 2000 (EP) .................................. 00125409

(51) Int. Cl.
*A61K 31/50* (2006.01)
*A61K 31/4965* (2006.01)
(52) U.S. Cl. .............. 514/247; 514/252.05; 514/254.09
(58) Field of Classification Search ................ 514/254, 514/373, 323, 254.09
See application file for complete search history.

(56) References Cited

U.S. PATENT DOCUMENTS

| | | | |
|---|---|---|---|
| 5,434,174 A | 7/1995 | Gidda et al. | |
| 5,532,241 A | 7/1996 | Böttcher et al. | |
| 5,576,321 A | 11/1996 | Krushinski, Jr. et al. | |
| 5,578,612 A | 11/1996 | Macor et al. | |
| 5,589,511 A | 12/1996 | Young et al. | |
| 5,912,256 A | 6/1999 | Koch et al. | |
| 6,310,068 B1 | 10/2001 | Böttcher et al. | |

FOREIGN PATENT DOCUMENTS

| | | |
|---|---|---|
| EP | 0 722 941 A | 7/1996 |
| EP | 0 736 525 A | 10/1996 |
| EP | 0 814 084 A | 12/1997 |
| GB | 2 222 768 A | 3/1990 |
| WO | WO 98 14433 A | 4/1998 |
| WO | WO 00 71549 A | 11/2000 |
| WO | WO 00 72832 A | 12/2000 |

OTHER PUBLICATIONS

C. Redillas et al., "Prophylactic pharmacological treatment of chronic daily headache"; Feb. 2000, 40 (2) 83-102.

Y.X. Wang et al., "Antinociceptive properties of fenfluramine, a serotonin reuptake inhibitor, in a rat model of neuropathy," Journal of Pharmacology and Experimental Therapeutics, (Dec. 1999) 291 (3) 1008-16.

*Primary Examiner*—Jennifer M Kim
(74) *Attorney, Agent, or Firm*—Millen, White, Zelano & Branigan, P.C.

(57) ABSTRACT

The present invention relates to the use of compounds being combined selective serotonin (5-HT) reuptake inhibitors (SSRIs) and 5-HT$_{1A}$ receptor agonists, in particular of 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, for the manufacture of a medicament for the treatment of chronic pain disorders or in treating other conditions where there is hyper-sensitization to painful signals, hyperalgesia, allodynia, enhanced pain perception, and enhanced memory of pain, as well as for the treatment of irritable bowel syndrome (IBS).

11 Claims, No Drawings

USE COMBINED 5-HT$_{1A}$ AGONISTS AND SELECTIVE SEROTONIN REUPTAKE INHIBITORS

The present invention relates to the use of compounds being combined selective serotonin (5-HT) reuptake inhibitors (SSRIs) and 5-HT$_{1A}$ receptor agonists for the manufacture of a medicament for the treatment of chronic pain.

Particularly, the present invention relates to the use of combined selective serotonin (5-HT) reuptake inhibitors (SSRIs) and 5-HT$_{1A}$ receptor agonists chosen from the group consisting of 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, for the manufacture of a medicament for the treatment of chronic pain.

1-[4-(5-Cyanoindol-3-yl)butyl]-4-(2-carbamoyl-benzofuran-5-yl)-piperazine, physiologically acceptable salts thereof (U.S. Pat. No. 5,532,241, column 7, lines 30 to 58) and a process (U.S. Pat. No. 5,532,241, Example 4) by which it/they can be prepared are known from U.S. Pat. No. 5,532,241. The compound which is referred to herein is described in the patent as a combined selective serotonin (5-HT) reuptake inhibitor (SSRIs) and 5-HT$_{1A}$ receptor agonist. Therefore, the use of 1-[4-(5-cyanoindol-3-yl)butyl]-4-(2-carbamoyl-benzofuran-5-yl)-piperazine and its physiologically acceptable acid addition salts for the manufacture of a medicament for the treatment of depressive disorders, including the sub-type disorders major depressive disorder and dysthymic disorder, for the treatment of anxiety disorders, for the treatment of psychiatric disorders like psychoses, schizophrenia or schizoaffective disorder, for the treatment of cerebral infarct like stroke and cerebral ischemia, for the treatment of CNS disorders such as tension, for the therapy of side-effects in the treatment of hypertension (e.g. with α-methyldopa) and for the prophylaxis and therapy of cerebral disorders is disclosed. Additionally, the use in endocrinology and gynecology is described, e.g. for the treatment of acromegaly, hypogonadism, secondary amenorrhea, premenstrual syndrome or undesired puerperal lactation.

3-{4-[4-(4-Cyano-phenyl)-piperazin-1-yl]-butyl}-1H-indole-5-carbonitrile, physiologically acceptable salts thereof (EP 0 736 525, page 3, lines 5, 26 and, page 8 lines 28 to page 9 lines 12) and a process (EP 0 736 525, Example 1) by which it/they can be prepared are known from EP 0 736 525. They show, in particular, actions on the central nervous system, especially 5-HT$_{1A}$-agonistic and 5-HT-reuptake inhibiting actions. Therefore they are suitable for the treatment of disorders of the central nervous system such as states of tension, depressions and/or psychoses and of side effects in the treatment of hypertension. Additionally, the use in endocrinology and gynecology is described, e.g. for the treatment of acromegaly, hypogonadism, secondary amenorrhea, premenstrual syndrome or undesired puerperal lactation, and furthermore for the prophylaxis and therapy of cerebral disorders, in particular in geriatrics, similarly to certein ergot alkaloids and for the control of the sequelae of cerebral infarcts (apoplexia cerebri), such as stroke and cerebral ischaemias.

The invention had the object of providing novel uses for compounds being combined selective serotonin (5-HT) reuptake inhibitors (SSRIs) and 5-HT$_{1A}$ receptor agonists, in particular of 1-[4-(5-cyanoindol-3-yl)butyl]-4-(2-carbamoyl-benzofuran-5-yl)-piperazine and its physiologically acceptable salts or 3-{4-[4-(4-cyano-phenyl)-piperazin-1-yl]-butyl}-1H-indole-5-carbonitrile or a physiologically acceptable salt thereof.

It has been found that combined selective serotonin (5-HT) reuptake inhibitors (SSRIs) and 5-HT$_{1A}$ receptor agonists, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, also have activity against pain, especially against chronic pain.

Piperazines, such as 1-[4-(5-cyanoindol-3-yl)butyl]-4-(2-carbamoyl-benzofuran-5-yl)-piperazine and its physiologically acceptable acid addition salts, are disclosed in U.S. Pat. No. 5,532,241 having analgesic effects. However, the usefulness of such piperazines for the treatment of pain, especially for chronic pain has not been disclosed.

The disclosed analgesic effects do not inevitably lead to effective treatments for chronic pain. Acute pain is a normal sensation triggered in the nervous system to alert an individual to possible injury. Chronic pain results from persistent pain signals in the nervous system which continue after the initial damage or injury has disappeared. Chronic pain can occur in the absence of any past injury or evidence of body damage, so-called psychogenic pain.

As used herein the term pain shall refer to all types of pain. Preferably, the term shall refer to all types of chronic pain including nociceptive, neuropathic, psychogenic pain, and mixed category pain (nociceptive and neuropathic components). This in particular includes, but is not limited to, diabetic neuropathy, neurogenic pain, central pain, somatic pain, visceral and cancer pain, inflammatory pain, post-operative pain, chronic low back pain, sciatica, cervical and lumbar pain, tension headaches, cluster headaches, chronic daily headaches, herpes neuralgia and post-herpetic neuralgia, facial and oral neuralgias and myofascial pain syndromes, phantom limb pain, stump pain and paraplegic pain, dental pain, opioid resistant pain, post-surgical pain including cardic surgery and mastectomy, pain of labour and delivery, post-partum pain, post-stroke pain, angina pain, genitourinary tract pain including pelvic pain and cystitis and vulvar vestibulitis and orchialgia, irritable bowel syndrome, pre-menstrual syndrome pain, pain resulting from burns or chemical injury or sunburn, and bone injury pain.

Sub-types of nociceptive pain are somatic pain and visceral pain. Somatic pain includes inflammatory pain, post-operative pain, chronic low back pain, cervical and lumber pain, cluster headaches, dental pain, pain of labour and delivery, postpartum pain, pain resulting from burns or chemical injury or sunburn, and bone injury pain. Visceral pain includes cancer pain, post-surgical pain including cardic surgery, angina pain, genito-urinary tract pain including pelvic pain and cystitis and vulvar vestibulitis and orchialgia and pre-menstrual pain syndrome. Sub-types of neuropathic pain are diabetic neuropathy, cancer pain, neurogenic pain, central pain, sciatica, herpes neuralgia, post-herpetic neuralgia, facial and oral neuralgias, phantom limb pain, stump pain and paraplegic pain, opioid-resistant pain, post-surgical pain including mastectomy and post-stroke pain. Sub-types of psychogenic pain are chronic daily headaches and tension headaches. Sub-types of mixed category pain are cancer pain, myofascial syndromes and tension headaches (e.g. McCaffery M, Pasero C. Pain:Clinical Manual p19 St. Louis: Mosby 1999; Merskek H and Bogduk (eds) Classification of chronic pain, second edition, IASP Task Force on Taxonomy, p 209-214, IASP Press, Seattle 1994; The Merck Manual, Section 14, Chapter 167, Pain, 17$^{th}$ Edition Merck & Co 1999).

The effectiveness of selective serotonin reuptake inhibitors (SSRIs) in various pain indications has been demonstrated in animals as well as humans.

For example, SSRIs have been shown to enhance the effects of traditional opioid analgesics and to be effective themselves against acute pain, inflammatory pain, and neuropathic pain in various animal models (e.g. Messing et al., Psychopharmacol. Commun. 1975, 1: 511-521; Hynes et al., Life Sci. 1985, 36: 2317-2323; Larsen and Arnt, Acta Pharmacol Toxicol. Copenh. 1985, 57: 345-351; Larsen and Hyttel, Acta Pharmacol Toxicol. Copenh. 1985, 57: 214-218; Yamamoto et al., Nippon Yakurigaku Zasshi 1989, 94: 189-206; Fasmer et al., Neuropharmacology 1989, 28: 1363-1366; Ardid et al., Fundam. Clin. Pharmacol. 1992, 6: 75-82; Akunne and Soliman, Pharmacol. Biochem. Behav. 1994, 48: 411-416; e.g. Schreiber et al., Eur. Neuropsychopharmacol. 1996, 6: 281-284; Korzeniewska et al., Pharmacol. Biochem. Behav. 1998, 59: 331-338; Luger et al., Pharmacol. Toxicol. 1999, 85: 263-268; Sawynok et al., Pain 1999, 82: 149-158; McCleane, Pain 2000, 85: 311-312).

SSRIs are also effective in experimental pain in healthy volunteers (Coquoz et al., Schweiz. Med. Wochenschr. 1991, 121: 1843-1845; Coquoz et al., Clin. Pharmacol. Ther. 1993, 54: 339-344) and, more relevant, in patients suffering of various chronic pain conditions like headache (tension headache), diabetic neuropathy, idiopathic pain, low back pain, phantom limb pain, rheumatic pain, irritable bowel syndrome, premenstrual syndrome pain or generalized or mixed pain syndrome (e.g. radicular pain, atypical facial pain) (e.g. Theesen and Marsh, DICP 1989, 23: 572-574; Sindrup et al., Pain 1990, 42: 135-144; Sindrup et al., Ther. Drug Monit. 1991, 13: 408-414; Petitto et al., Psychosomatics 1992, 33: 338-341; Boyer, Int. Clin. Psychopharmacol. 1992, 6 (suppl. 5); 5-12; Power-Smith and Turkington, Br. J. Psychiatry 1993, 163: 105-106; Manna et al., Headache 1994, 34: 44-49; Langemark and Olesen, Headache 1994, 34: 20-24; Finley, Ann. Pharmacother. 1994; 28: 1359-1369; Saper et al., Headache 1994, 34: 497-502; Gruber et al., Psychiatr. Clin. North Am. 1996,19: 351-369; Rani et al., Aneth. Analg. 1966, 83: 371-375; McQuay et al., Pain 1996, 68: 217-227; Jung et al., J. Gen. Intern. Med. 1997, 12: 384-389; Abramson and Garfin, Pain 1999, 83: 137-145; Baraczka et al., Orv. Hetil. 1997, 138: 2605-2607; O'Mally et a., J. Fam. Pract. 1999, 48: 980-990; Ciaramella et al., Minerva Anestesiol. 2000, 66: 55-61; Ansari, Harv. Rev. Psychiatry 2000, 7: 257-277).

Moreover, SSRIs are the most frequent drugs used in depressive disorders, and there is a high comorbidity for depression and pain, and they may even share a common etiology (e.g. Ekselius et al., Scand. J. Rehabil. Med. 1997, 29: 91-96; Max et al., N. Engl. J. Med. 1992, 326: 1250-1256; Gruber et al., Psychiatr. Clin. North Am. 1996,19: 351-369).

Finally, selective serotonin 5-$HT_{1A}$ receptor agonists reduce pain in animals in acute and chronic pain and inflammatory pain models (e.g. Fasmer et al., Pharmacol. Biochem Behav. 1986, 25: 883-888; Bragin et al., Pain 1989, 36: 257-261; Giordano and Rogers, Pain 1989, 39: 109-113; Murphy and Zemlan, Neuropharmacology 1990, 29: 463-468; Crisp et al., Gen. Pharmacol. 1991, 22: 247-251; Danzebrink and Gebhart, Brain Res. 1991, 538: 64-75; Eide and Hole, Neuropharmacology 1991, 30: 727-731; Giordano and Rogers, Pain 1992, 50: 365-372; Mjellem et al., Neuroreport 1992, 3: 1061-1064; Eide and Hole, Cephalagia 1993, 13: 75-85; Korneyev and Seredenin, Life Sci. 1993, 52: 997-1004; Cervo et al., Eur. J. Pharmacol. 1994, 263:187-191; Xu et al., J. Pharmacol. Exp. Ther. 1994, 269: 1182-1189; Sanchez et al., Neuroreport 1995, 6: 2585-2588; Millan et al., Behav. Brain Res. 1996, 73: 69-77; Robles et al., Eur. J. Pharmacol. 1996, 295: 181-188; Galeotti et al., Pharmacol. Biochem. Behav. 1997, 57: 835-841; Rouzade et al., Digest. Dis. Sci. 1998, 43: 2048-2054; Jain and Kulkarni, Meth. Find. Exp. Clin. Pharmacol. 1999, 21: 161-165; Shannon and Lutz, Psychopharmacology 2000, 149: 93-97). To our knowledge, clinical results in pain patients are not available due to the lack of selective 5-$HT_{1A}$ agonists on the market.

Therefore, the combination of serotonin reuptake inhibiting properties and serotonin 5-$HT_{1A}$ agonistic properties as realized in 1-[4-(5-cyanoindol-3-yl)butyl]-4-(2-carbamoyl-benzofuran-5-yl)-piperazine and its salts thereof or 3-{4-[4-(4-cyano-phenyl)-piperazin-1-yl]-butyl}-1H-indole-5-carbonitrile and its salts thereof represents an advantage over SSRIs alone for the treatment of chronic pain disorders or in treating other conditions where there is hyper-sensitization to painful signals, hyperalgesia, allodynia, enhanced pain perception, and enhanced memory of pain.

Accordingly, the present invention relates to the use of compounds being combined selective serotonin (5-HT) reuptake inhibitors (SSRIs) and 5-$HT_{1A}$ receptor agonists for the manufacture of a medicament for the treatment of chronic pain.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of chronic pain.

The present invention relates furthermore to the use of 3-{4-[4-(4-cyano-phenyl)-piperazin-1-yl]-butyl}-1H-indole-5-carbonitrile or a physiologically acceptable salt thereof, for the manufacture of a medicament for the treatment of chronic pain.

A preferred salt of 1-[4-(5-cyanoindol-3-yl)butyl]-4-(2-carbamoyl-benzofuran-5-yl)-piperazine is 1-[4-(5-cyanoindol-3-yl)butyl]-4-(2-carbamoyl-benzofuran-5-yl)-piperazine hydrochloride. Therefore the invention relates to the use for the manufacture of a medicament for the treatment of chronic pain in which the pharmacologically acceptable salt of 1-[4-(5-cyanoindol-3-yl)butyl]-4-(2-carbamoyl-benzofuran-5-yl)-piperazine is 1-[4-(5-cyanoindol-3-yl)butyl]-4-(2-carbamoyl-benzofuran-5-yl)-piperazine hydrochloride.

A preferred salt of 3-{4-[4-(4-cyano-phenyl)-piperazin-1-yl]-butyl}-1-H-indole-5-carbonitrile is 3-{4-[4-(4-cyano-phenyl)-piperazin-1-yl]-butyl}-1H-indole-5-carbonitrile hydrochloride.

Therefore the invention relates to the use for the manufacture of a medicament for the treatment of chronic pain in which the pharmacologically acceptable salt of 3-{4-[4-(4-cyano-phenyl)-piperazin-1-yl]-butyl}-1H-indole-5-carbonitrile is 3-{4-[4-(4-cyano-phenyl)-piperazin-1-yl]-butyl}-1H-indole-5-carbonitrile hydrochloride.

Additionally, the invention relates to the use of a pharmaceutical composition containing at least a compound being a combined selective serotonin (5-HT) reuptake inhibitor (SSRI) and 5-$HT_{1A}$ receptor agonist, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, together with at least one solid, liquid or semiliquid excipient or adjunct for the treatment of chronic pain.

Thus the invention provides a pharmaceutical preparation for the treatment of pain characterized in that it contains at least 1-[4-(5-cyanoindol-3-yl)butyl]-4-(2-carbamoyl-benzofuran-5-yl)-piperazine or one of its pharmaceutically acceptable salts.

Thus the invention provides a pharmaceutical preparation for the treatment of pain characterized in that it contains at least 3-{4-[4-(4-cyano-phenyl)-piperazin-1-yl]-butyl}-1H-indole-5-carbonitrile or one of its pharmaceutically acceptable salts.

The compounds being combined selective serotonin (5-HT) reuptake inhibitors (SSRIs) and 5-HT$_{1A}$ receptor agonists according to the invention are preferably administered in analogy to other known commercially available preparations for the treatment of pain (e.g. duloxetine). A unit dose will generally contain from 0.1 to 1000 mg, preferably between approximately 0.1 and 500 mg, in particular 5, 10, 20, 30, 40, 50, 100, 150, 200, 250 and 300 mg. The composition may be administered once or more times a day for example 2, 3 or 4 times daily. The daily dose is preferably between approximately 0.01 and 50 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

It is preferred that the chronic pain to be treated by combined selective serotonin (5-HT) reuptake inhibitors (SSRIs) and 5-HT$_{1A}$ receptor agonists, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, is nociceptive pain. Preferred indications of nociceptive pain are inflammatory and post-operative pain.

Therefore, the invention relates to the use of compounds being combined selective serotonin (5-HT) reuptake inhibitors (SSRIs) and 5-HT$_{1A}$ receptor agonists, in particular of 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, for the manufacture of a medicament for the treatment of nociceptive pain.

It is preferred that the chronic pain to be treated by combined selective serotonin (5-HT) reuptake inhibitors (SSRIs) and 5-HT$_{1A}$ receptor agonists, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, is neuropathic pain. Preferred indications of neuropathic pain are neurogenic pain and facial and oral neuralgias.

Therefore, the invention relates to the use of compounds being combined selective serotonin (5-HT) reuptake inhibitors (SSRIs) and 5-HT$_{1A}$ receptor agonists, in particular of 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, for the manufacture of a medicament for the treatment of neuropathic pain.

It has additionally been found that combined selective serotonin (5-HT) reuptake inhibitors (SSRIs) and 5-HT$_{1A}$ receptor agonists, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, are further useful in treating other conditions where there is hyper-sensitization to painful signals, hyperalgesia, allodynia, enhanced pain perception, and enhanced memory of pain. A preferred indication is irritable bowel syndrome.

Irritable bowel syndrome (IBS) is a common disorder of the intestines that leads to crampy pain, gassiness, bloating, and changes in bowel habits. The cause of IBS is not known but it often has been thought to be caused by emotional conflict or stress. IBS is called a functional disorder because there is no sign of disease when the colon is examined. People suffering from IBS usually have crampy abdominal pain with painful constipation or diarrhea.

Therefore, the invention relates to the use of compounds being combined selective serotonin (5-HT) reuptake inhibitors (SSRIs) and 5-HT$_{1A}$ receptor agonists, in particular of 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, for the manufacture of a medicament for the treatment of inflammatory bowel syndrome.

A preferred salt of 1-[4-(5-cyanoindol-3-yl)butyl]-4-(2-carbamoyl-benzofuran-5-yl)-piperazine is 1-[4-(5-cyanoindol-3-yl)butyl]-4-(2-carbamoyl-benzofuran-5-yl)-piperazine hydrochloride.

Therefore the invention relates to the use for the manufacture of a medicament for the treatment of irritable bowel syndrome in which the pharmacologically acceptable salt of 1-[4-(5-cyanoindol-3-yl)butyl]-4-(2-carbamoyl-benzofuran-5-yl)-piperazine is 1-[4-(5-cyanoindol-3-yl)butyl]-4(2-carbamoyl-benzofuran-5-yl)-piperazine hydrochloride.

A preferred salt of 3-{4-[4-(4-cyano-phenyl)-piperazin-1-yl]-butyl}-1H-indole-5-carbonitrile is 3-{4-[4-(4-cyano-phenyl)-piperazin-1-yl]-butyl}-1H-indole-5-carbonitrile hydrochloride.

Therefore the invention relates to the use for the manufacture of a medicament for the treatment of irritable bowel syndrome in which the pharmacologically acceptable salt of 3-{4-[4-(4-cyano-phenyl)-piperazin-1-yl]-butyl}-1H-indole-5-carbonitrile is 3-{4-[4-(4-cyano-phenyl)-piperazin-1-yl]-butyl}-1H-indole-5-carbonitrile hydrochloride.

Additionally, the invention relates to the use of a pharmaceutical composition containing at least a compound being a combined selective serotonin (5-HT) reuptake inhibitor (SSRI) and 5-HT$_{1A}$ receptor agonist, in particular 1-[4-(5-cyanoindol-3-yl)butyl]-4-(2-carbamoyl-benzofuran-5-yl)-piperazine or a physiologically acceptable salt thereof or 3-{4-[4-(4-cyano-phenyl)-piperazin-1-yl]-butyl}-1H-indole-5-carbonitrile or a physiologically acceptable salt thereof, together with at least one solid, liquid or semiliquid excipient or adjunct for the treatment of irritable bowel syndrome.

Thus the invention provides a pharmaceutical preparation for the treatment of irritable bowel syndrome characterized in that it contains at least 1-[4-(5-cyanoindol-3-yl)butyl]-4-(2-carbamoyl-benzofuran-5-yl)-piperazine or one of its pharmaceutically acceptable salts.

Thus the invention provides a pharmaceutical preparation for the treatment of irritable bowel syndrome characterized in that it contains at least 3-{4-[4-(4-cyano-phenyl)-piperazin-1-yl]-butyl}-1H-indole-5carbonitrile or one of its pharmaceutically acceptable salts.

The compounds being combined selective serotonin (5-HT) reuptake inhibitors (SSRIs) and 5-HT$_{1A}$ receptor agonists according to the invention are preferably administered in analogy to other known commercially available preparations for the treatment of irritable bowel syndrome (IBS). A unit dose will generally contain from 0.1 to 1000 mg, preferably between approximately 0.1 and 50 mg, in particular 5, 10 and 20 mg. The composition may be administered once a day. The daily dose is preferably between approximately 0.01 and 10 mg/kg of body weight.

However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also per-oral routes of administration (e.g. intraveneous or transdermal) can be utilized.

The pharmaceutical preparations used for the treatment of pain or preferred for IBS, can be used as pharmaceuticals in human or veterinary medicine.

A process for the manufacture of a pharmaceutical preparation used for the treatment of chronic pain is characterised in that one compound being combined selective serotonin (5-HT) reuptake inhibitor (SSRI) and $5\text{-HT}_{1A}$ receptor agonist chosen from the group consisting of 1-[4-(5-cyanoindol-3-yl)butyl]-4-(2-carbamoyl-benzofuran-5-yl)-piperazine or a physiologically acceptable salt thereof or 3-{4-[4-(4-cyanophenyl)-piperazin-1-yl]-butyl}-1H-indole-5-carbonitrile or a physiologically acceptable salt thereof, are converted into a suitable dosage form together with at least one solid, liquid or semiliquid excipient or adjunct.

Suitable excipients are organic or inorganic substances which are suitable for enteral (e.g. oral), parenteral or topical adminstration and which do not react with 1-[4-(5-cyanoindol-3-yl)butyl]-4-(2-carbamoyl-benzofuran-5-yl)-piperazine and/or one of its biocompatible salts, for example water, vegetable oils, benzyl alcohols, alkylene glycols, polyethylene glycols, glycerol triacetate, gelatine, carbohydrates such as lactose or starch, magnesium stearate, talc, petroleum jelly. Forms which are used for oral administration are, in particular, tablets, pills, sugar-coated tablets, capsules, powders, granules, syrups, liquids or drops, forms for rectal administration are, in particular suppositories, forms for parenteral administration are, in particular, solvents, preferably oily or aqueous solutions, furthermore suspensions, emulsions or implants, and forms for topical administration are transdermal plasters, ointments, creams or powders. 1-[4-(5-cyanoindol-3-yl)butyl]-4-(2-carbamoyl-benzofuran-5-yl)-piperazine and/or one of its pharmaceutically acceptable salts may also be lyophilized and the resulting lyophilisates used for example for the preparation of injectable products. The abovementioned preparations can be in sterilized form and/or comprise auxiliaries such as glidants, preservatives, stabilizers and/or wetting agents, emulsifiers, salts for modifying the osmotic pressure, buffer substances, colourings, flavourings and/or other active ingredients, e.g. one or more vitamins.

Preparations may, if desired, be designed to give slow release of 1-[4-(5-cyanoindol-3-yl)butyl]-4-(2-carbamoyl-benzofuran-5-yl)-piperazine or a biocompatible salt thereof.

The following examples relate to animal models which are useful for illustrating the effectiveness of combined $5\text{-HT}_{1A}$ agonists and serotonin reuptake inhibitors.

EXAMPLE 1

Procedures in the Mouse and the Rat to Test Pain-Relieving Acute Analgetic Properties 1. Hot plate test in mouse or rat according to Eddy and Leimbach (J. Pharmacol. Exp. Ther. 1953, 107: 385-393):

Mice or rats are placed onto a hot metal plate maintained at 54° C. for mice or 52° C. for rats surrounded by a Plexiglas cylinder (Height: 13 cm; Diameter: 19 cm). The latency to the first foot-lick is measured (maximum: 30 seconds).

2. Tail flick test in mouse or rat according to by D'Amour and Smith (J. Pharmacol. Exp. Ther. 1941, 72: 74-79):

The animal's tail is heated by means of a thermal light source. The latency before the animal withdraws its tail is measured (maximum: 15 seconds for mice, 30 seconds for rats).

3. Shock sensitivity test in the mouse or rat follows that described by Eschalier et al. (Eur. J. Pharmacol. 1981, 74: 1-7):

Each animal is placed on a grid floor connected to an electric shock generator that transmits a brief electric shock to the animal's paws. Three shocks are given at an intensity of 1 mA, each for a duration of 0.5 sec. The shocks are spaced at 30 second intervals. Response to electric shock is quantified using a scale incorporating three parameters: jump, vocalization and flight (each parameter is scored 0, 1 or 2). The total score obtained for all three parameters for the three shocks is taken as a measure of sensitivity to electric shock.

4. Shock Titration Test in the rat according to Weiss and Laties (J. Pharmacol. Exp. Ther. 1961, 131: 120-129):

The apparatus consists of a sound-attenuated standard Skinner Box (23×21×18 cm) fitted with a house light, one lever and a grid floor connected to a programmable scrambled shock generator (Imetronic). The Skinner boxes are connected to a MED.PC programming system which controls the experiment and collected the data automatically. The rats are first trained to press a lever in the experimental chamber in order to stop an electric foot-shock (0.8 mA) administered at 5 second intervals (escape training). They are then trained to control the intensity of the electric shock (30 graded steps: 0.03-0.9 mA) by pressing the lever. When the rat presses the lever in the presence of shock, the shock terminates and returns 5 seconds later at the next lower intensity. If the rat fails to respond during the shock presentation, the shock terminates automatically after 5 seconds and returns 5 seconds later at the next higher intensity (shock titration). Lever pressing between shocks (inter-trial responses) is without consequence. Each training sessions lasts 15 minutes and begins at the tenth intensity level (0.3 mA). The animals receive a administration of the vehicle of the test compound 60 minutes before each session. Two behavioral measures are taken: The median shock level (nociceptive threshold) per rat is defined as the intensity above and below which the animal receives 50% of its shocks, and the Inter-trial responses defined as the number of lever-presses occurring between shock presentations. Drug testing is performed on animals having reached stable baseline performance over two consecutive weeks. Drug testing sessions are given twice weekly with at least one training session without drugs between drug test sessions. Animals are tested (training and test sessions) 5 days per week (Monday to Friday). As above, sessions terminate after 15 minutes. Each animal is used as its own control and receives all the selected treatments and controls (vehicle) in separate testing sessions. The sequence of treatments is determined by a procedure to ensure even distribution of the different treatments in time. Each animal is always tested in the same Skinner Box, in the same order and at the same time of the day.

5. Phenylbenzoquinone and acetic writhing tests in mice follow the methods described by Hendershot et al (J. Pharmacol. Exp. Ther. 1959, 125: 237-240):

Mice are injected with phenylbenzoquinone (PBQ) (1.25 mg/kg i.p.) or acetic acid (0.5% i.p.). This treatment induces a recognizable writhing response in control animals. The number of writhes is counted for 10 minutes beginning 5 minutes after injection of PBQ or acetic acid.

1-[4-(5-cyanoindol-3-yl)butyl]-4-(2-carbamoyl-benzofuran-5-yl)-piperazine hydrochloride at 30 mg/kg p.o. reduced writhes by 82%.

EXAMPLE 2

Procedures in the Mouse and the Rat to Test Pain-Relieving Properties Associated with Antiinflammatory Processes 1. Formalin paw test in the mouse or rat accorrding to Wheeler-Aceto et al., (Psychopharmacology 1991, 104: 35-44):

Animals are given an intraplantar injection of 5% formalin (25 µl for the mouse, 50 µl for the rat) into the posterior left paw. This treatment induces a recognizable flinching response in control animals. The number of flinches is counted for 10 minutes, beginning immediately after injection of formalin (early phase) and again for 5 minutes in mice or 15 minutes in rats, beginning 20 minutes after the injection.

1-[4-(5-cyanoindol-3-yl)butyl]-4-(2-carbamoyl-benzofuran-5-yl)-piperazine hydrochloride at 30 mg/kg p.o. reduced the formalin-induced pain response by 79%.

EXAMPLE 3

Procedures in Mouse and Rat to Test Pain-Relieving Properties Associated with Antiinflammatory Processes and Antiinflammatory/Antipyretic Properties 1. Carrageenan Edema Test in the rat follows that described by Winter et al. (Proc. Soc. Exp. Biol. Med. 1962, 111: 544-547):

Animals are injected with a carrageenan solution into the lower surface of the right hind-paw (0.75 mg per paw in 0.05 ml physiological saline). 2 hours later rats are submitted consecutively to thermal and tactile stimulation of both the non-inflamed and the inflamed hindpaws. For thermal stimulation, the apparatus (Ugo Basile, Reference: 7371) consists of 6 individual Plexiglas boxes (17×11×13 cm) placed upon an elevated glass floor. A rat is placed in the box and left free to habituate for 10 minutes. Then, a mobile infrared radiant source (setting 20) is focused under the non-inflamed and inflamed hindpaws and the paw-withdrawal latencies are automatically recorded. Paw-withdrawal interrupts the reflected radiation and switches off the counter and the light source. In order to prevent tissue damage, if no reaction is noted, the test is terminated after 45 seconds. For tactile stimulation, the animal is placed under an inverted Plexiglas box (17×11×13 cm) on a grid floor. The tip of an electronic Von Frey probe is then applied with increasing pressure to the non-inflamed and inflamed hindpaws and the force required to induce paw-withdrawal is automatically recorded. This procedure is carried out 3 times and the mean force per paw is calculated to provide basic scores per animal. 3.5 hours later, the animals are sacrificed by a blow to the cervical vertebrae and the hind-paws sectioned and weighed. An increase in paw weight (edema) indicates inflammation. This later procedure can also be appiled to mice.

2. Yeast Hyperthermia Test in the mouse or rat according to by Teotino et al (J. Med. Chem. 1963, 6: 248):

Animals are first measured for rectal temperature using a rectal probe. They are then injected with a yeast suspension (512 mg/kg s.c.). 8 hours later, the test substance is administered. Mice are measured for rectal temperature immediately before test substance administration and again 60 and 120 minutes later.

EXAMPLE 4

Procedures in Rats to Test Pain-Releaving Properties in Chronic Pain and Inflammation 1. Chronic inflammatory pain test (Freund's adjuvant test) in the rat according to Whiteley (Current Protocols in Pharmacology, Wiley, N.Y., 5.5, 1999):

An injection of Freund's adjuvant in rats induces chronic clinical signs of polyarthritis with pain. On Day 1, rats are weighed and injected intradermally with a suspension of *Mycobacterium butyricum* (Freund's adjuvant) into the proximal quarter of the tail (1 mg in 0.1 ml mineral oil). Sham controls receive a similar injection of mineral oil. On Day 18, when the chronic state is fully installed, rats are weighed again and are evaluated for clinical symptoms of inflammation. They are then submitted consecutively to thermal and tactile stimulation of both hindpaws. For the clinical signs, each paw is scored for inflammation according to a 5-point scale (0-4) and the tail according to a 4-point scale (0-3), i.e. a maximum score of 19 per animal. For thermal stimulation, the apparatus (Ugo Basile, Reference: 7371) consists of 6 individual Plexiglas boxes (17×11×13 cm) placed upon an elevated glass floor. A rat is placed in the box and left free to habituate for 10 minutes. Then, a mobile infrared radiant source (setting 20) is focused under each hindpaw and the paw-withdrawal latency is automatically recorded. Paw-withdrawal interrupts the reflected radiation and switches off the counter and the light source. In order to prevent tissue damage, if no reaction is noted, the test is terminated after 45 seconds. For tactile stimulation, the animal is placed under an inverted Plexiglas box (17×11×13 cm) on a grid floor. The tip of an electronic Von Frey probe (Bioseb, Model 1610) is then applied with increasing pressure to each hindpaw and the force required to induce paw-withdrawal is automatically recorded. This procedure is carried out 3 times and the mean force per paw is calculated to provide basic scores per animal. Prior to receiving drug treatment all animals will be submitted to tactile stimulation and assigned to treatment groups matched on the basis of their pain response.

2. Neuropathic pain test (Chung test) in the rat according to Kim and Chung (Pain 1992, 50: 355-363):

Tight ligature of spinal nerves in rats is associated with hyperalgesia, allodynia and spontaneous pain, and constitutes therefore a model for peripheral neuropathic pain in humans. Antihyperalgesics reduce these chronic signs of pain hypersensitivity. Rats (180-220 g) are anesthetized (sodium pentobarbital 40 mg/kg i.p.) and an incision at the L4-S2 level is performed to expose the left L5 and L6 spinal nerves. A ligature is tied tightly around each nerve. The wound is then sutured. The rats receive an i.m. injection of 50 000 IU Penicilline and are allowed to recover. At least 2 weeks after the surgery, when the chronic state is fully installed, rats are submitted consecutively to thermal and tactile stimulation of both the non-lesioned and the lesioned hindpaws. For thermal stimulation, the apparatus consists of 6 individual Plexiglas boxes (17×11×13 cm) placed upon an elevated glass floor. A rat is placed in the box and left free to habituate for 10 minutes. Then, a mobile infrared radiant source (setting 20) is focused under the non-lesioned and lesioned hindpaws and the paw-withdrawal latencies are automatically recorded. Paw-withdrawal interrupts the reflected radiation and switches off the counter and the light source. In order to prevent tissue damage, if no reaction is noted, the test is terminated after 45 seconds. For tactile stimulation, the animal is placed under an inverted Plexiglas box (17×11×13 cm) on a grid floor. The tip of an electronic Von Frey probe is then applied with increasing pressure to the non-lesioned and lesioned hindpaws and the force required to induce paw-withdrawal is automatically recorded. This procedure is carried out 3 times and the mean force per paw is calculated to provide basic scores per animal. Prior to receiving drug treatment all animals will be submitted to tactile stimulation and assigned to treatment groups matched on the basis of their pain response.

The Examples Which Follow Relate to Pharmaceutical Products:

EXAMPLE A

Vials

A solution of 100 g of a compound being combined selective serotonin (5-HT) reuptake inhibitor (SSRI) and 5-$HT_{1A}$ receptor agonist and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

EXAMPLE B

Suppositories

A mixture of 20 g of a compound being combined selective serotonin (5-HT) reuptake inhibitor (SSRI) and 5-$HT_{1A}$ receptor agonist is melted with 100 g of soya lecithin and 1400 g of cocoa butter, and the mixture is poured into moulds and left to cool. Each suppository comprises 20 mg of active ingredient.

EXAMPLE C

Solution

A solution is prepared from 1 g of a compound being combined selective serotonin (5-HT) reuptake inhibitor (SSRI) and 5-$HT_{1A}$ receptor agonist, 9.38 g of $NaH_2PO_4.2H_2O$, 28.48 g of $Na_2HPO_4.12H_2O$ and 0.1 g of benzalkonium chloride in 940 ml of twice-distilled water. The pH is brought to 6.8, and the solution is made up to 1 l and sterilized by irradiation. This solution can be used in the form of eyedrops.

EXAMPLE D

Ointment 500 mg of a compound being combined selective serotonin (5-HT) reuptake inhibitor (SSRI) and 5-$HT_{1A}$ receptor agonist are mixed with 99.5 g of petroleum jelly under aseptic conditions.

EXAMPLE E

Tablets

A mixture of 1 kg of a compound being combined selective serotonin (5-HT) reuptake inhibitor (SSRI) and 5-$HT_{1A}$ receptor agonist, 4 kg of lactose, 1.2 kg of potato starch, 0.2 kg of talc and 0.1 kg of magnesium stearate is tableted in the customary manner in such a way that each tablet comprises 10 mg of active ingredient.

EXAMPLE F

Sugar-Coated Tablets

A mixture is tableted analogously to Example E, and the tablets are subsequently coated in the customary manner with a coating of sucrose, potato starch, talc, tragacanth and colouring.

EXAMPLE G

Capsules 2 kg of a compound being combined selective serotonin (5-HT) reuptake inhibitor (SSRI) and 5-$HT_{1A}$ receptor agonist are filled into hard gelatin capsules in the customary manner so that each capsule comprises 20 mg of the active ingredient.

EXAMPLE H

Ampoules

A solution of 1 kg of a compound being combined selective serotonin (5-HT) reuptake inhibitor (SSRI) and 5-$HT_{1A}$ receptor agonist in 60 l of twice-distilled water is filter-sterilized, filled into ampoules, lyophilized under sterile conditions and sealed in sterile form. Each ampoule comprises 10 mg of active ingredient.

EXAMPLE I

Spray for Inhalation 14 g of a compound being combined selective serotonin (5-HT) reuptake inhibitor (SSRI) and 5-$HT_{1A}$ receptor agonist are dissolved in 10 l of isotonic NaCl solution, and the solution is filled into commercially available pump-operated spray containers. The solution can be sprayed into mouth or nose. One actuation (approximately 0.1 ml) corresponds to a dose of approximately 0.14 mg.

The invention claimed is:

1. A method for the treatment of irritable bowel syndrome, comprising administering to a host in need thereof an agent having combined selective serotonin (5-HT) reuptake inhibitor (SSRIs) and 5-$HT_{1A}$ receptor agonist activity, said agent comprising:
1-[4-(5-cyanoindol-3-yl)butyl]-4-(2-carbamoyl-benzofuran-5-yl)-piperazine, or
3-{4-[4-(4-cyano-phenyl)-piperazin-1-yl]butyl}-1H-indole-5-carbonitrile, or a physiologically acceptable salt thereof.

2. A method according to claim 1, wherein the physiologically acceptable salt of 1-(4-5-cyanoindol-3-yl)butyl -4-(2-carbamoyl-benzofuran-5-yl)-piperazine is 1-[4-(5-cyanoindol-3-yl)butyl]-4-(2-carbamoyl-benzofuran-5-yl)-piperazine hydrochloride.

3. A method according to claim 1, wherein the physiologically acceptable salt of 3- {4-[4-(4-cyano-phenyl)-piperazin-1-yl]-butyl}-1H-indole-5-carbonitrile is 3-{4-[4-(4-cyano-phenyl)-piperazin-1-yl]-butyl}-1H-indole-5-carbonitrile hydrochloride.

4. A method according to claim 1, comprising administering said agent to said host to reduce crampy pain, gassiness, bloating, abdominal strain, constipation, or diarrhea associated with irritable bowel syndrome.

5. A method according to claim 1, comprising administering said agent at a unit dose of 0.1 to 1000 mg.

6. A method according to claim 1, comprising administering said agent at a daily dose of 0.01 to 10 mg/kg of body weight of said host.

7. A method according to claim 1, comprising administering a pharmaceutical composition, which comprises the agent having combined selective serotonin (5-HT) reuptake inhibitor (SSRIs) and 5-$HT_{1A}$ receptor agonist activity and a physiologically acceptable carrier.

8. A method according to claim 1, comprising administering said agent orally or perorally to said host.

9. A method according to claim 7, comprising administering said pharmaceutical composition orally or perorally to said host.

10. A method according to claim 1, wherein 1-[4-(5-cyanoindol-3-yl)butyl]-4-(2-carbamoyl-benzofuran-5-yl)-piperazine or a physiologically acceptable salt thereof is administered.

11. A method according to claim 1, wherein 3-{4-[4-(4-cyano-phenyl)-piperazin-1-yl]butyl }-1H-indole-5-carbonitrile or a physiologically acceptable salt thereof is administered.

* * * * *